United States Patent
Chau

(10) Patent No.: US 10,568,803 B2
(45) Date of Patent: Feb. 25, 2020

(54) MULTI-PURPOSE HEALTHCARE APPARATUS

(71) Applicant: Gold Crown Investment Limited, Hong Kong (HK)

(72) Inventor: Yiu Wing Chau, Hong Kong (HK)

(73) Assignee: GOLD CORWON INVESTMENT LIMITED, Hong Kong (CN)

( * ) Notice: Subject to any disclaimer, the term of this patent is extended or adjusted under 35 U.S.C. 154(b) by 1033 days.

(21) Appl. No.: 14/907,564

(22) PCT Filed: Aug. 29, 2013

(86) PCT No.: PCT/CN2013/082570
§ 371 (c)(1),
(2) Date: Jan. 25, 2016

(87) PCT Pub. No.: WO2015/027434
PCT Pub. Date: Mar. 5, 2015

(65) Prior Publication Data
US 2016/0175183 A1 Jun. 23, 2016

(51) Int. Cl.
*A61H 7/00* (2006.01)
*A45D 34/04* (2006.01)
(Continued)

(52) U.S. Cl.
CPC .............. *A61H 7/003* (2013.01); *A45D 19/02* (2013.01); *A45D 34/00* (2013.01); *A45D 34/04* (2013.01);
(Continued)

(58) Field of Classification Search
CPC ........ A61H 7/002; A61H 7/003; A61H 19/44; A61H 2201/102; A61H 2201/105;
(Continued)

(56) References Cited

U.S. PATENT DOCUMENTS 4,925,327 A * 5/1990 Wirt .................... A61M 35/006
401/132
5,597,255 A * 1/1997 Yager .................... A45D 34/04
401/205
(Continued)

FOREIGN PATENT DOCUMENTS

CN 1054363 A 9/1991
CN 1098323 A 2/1995
(Continued)

OTHER PUBLICATIONS

International Search Report for PCT Application No. PCT/CN2013/082570 dated Aug. 29, 2013.
(Continued)

*Primary Examiner* — Timothy A Stanis
(74) *Attorney, Agent, or Firm* — Spruson & Ferguson (Hong Kong) Limited

(57) ABSTRACT

The present invention provides an interchangeable multi-purpose healthcare apparatus comprising silicate-based ceramic materials containing tourmaline, said apparatus comprising a cylindrical bottle body (101) and different functional heads for different purposes. A top open end of said cylindrical bottle body is configured with a screw-type bottleneck (103) for connecting different functional heads according to different needs of the user. The present apparatus takes advantages of the far infrared ray, microcurrent and negative ions matching human bioelectricity which are emitted and transmitted by the silicate-based ceramic materials containing tourmaline, in association with the addition of liquids of different temperatures as massage medium, to allow suitable temperature adjustment of the user. Massage medium being functionalized by the tourmaline-containing ceramics can also be beneficial to human body. In combination with different functional heads and auxiliary materi-
(Continued)

als, the present apparatus becomes a personalized and specialized apparatus for massage and auxiliary health care.

10 Claims, 7 Drawing Sheets

(51) Int. Cl.
A61H 23/06 (2006.01)
A61M 35/00 (2006.01)
A45D 19/02 (2006.01)
A45D 40/24 (2006.01)
A45D 34/00 (2006.01)
A61H 19/00 (2006.01)

(52) U.S. Cl.
CPC ............ *A45D 40/24* (2013.01); *A61H 7/002* (2013.01); *A61H 19/44* (2013.01); *A61H 23/06* (2013.01); *A61M 35/003* (2013.01); *A45D 2034/002* (2013.01); *A45D 2034/007* (2013.01); *A45D 2200/202* (2013.01); *A61H 2201/0153* (2013.01); *A61H 2201/0207* (2013.01); *A61H 2201/10* (2013.01); *A61H 2201/102* (2013.01); *A61H 2201/105* (2013.01); *A61H 2201/1253* (2013.01); *A61H 2201/1685* (2013.01)

(58) Field of Classification Search
CPC .... A61H 2201/0153; A61H 2201/1685; A45D 40/24; A45D 34/00; A45D 34/04
See application file for complete search history.

(56) References Cited

U.S. PATENT DOCUMENTS

| | | | | |
|---|---|---|---|---|
| 6,488,665 B1* | 12/2002 | Severin | ................. | A01N 59/12 401/132 |
| 8,348,913 B2* | 1/2013 | Hoang | ................... | A45D 34/04 604/310 |
| 2005/0045742 A1 | 3/2005 | Nakamura | | |
| 2006/0058714 A1* | 3/2006 | Rhoades | .............. | A45D 24/007 601/73 |
| 2011/0103878 A1* | 5/2011 | Neuner | ................... | A45D 34/04 401/203 |
| 2013/0323321 A1* | 12/2013 | Garcia | ..................... | A61Q 5/02 424/600 |
| 2014/0234004 A1* | 8/2014 | Thorpe | .................. | A45D 34/04 401/1 |
| 2018/0056012 A1* | 3/2018 | Vidal | ................... | A61M 11/006 |

FOREIGN PATENT DOCUMENTS

| | | |
|---|---|---|
| CN | 1124166 A | 6/1996 |
| CN | 101214190 A | 7/2008 |
| CN | 201376740 Y | 1/2010 |
| CN | 101693631 A | 4/2010 |
| CN | 201619738 U | 11/2010 |
| CN | 102078663 A | 6/2011 |
| CN | 102503363 A | 6/2012 |
| CN | 202776947 U | 3/2013 |
| CN | 103083174 A | 5/2013 |
| JP | 2004269483 A | 9/2004 |
| JP | 2004352257 A | 12/2004 |
| JP | 2005325238 A | 11/2005 |
| WO | 2007024060 A1 | 3/2007 |
| WO | 2010141159 A9 | 12/2010 |

OTHER PUBLICATIONS

Chen et al., The Characterization and Planting Application of Tourmaline, Journal of Far East University vol. 27 No. 4, Taiwan, Dec. 2010.

* cited by examiner

MULTI-PURPOSE HEALTHCARE APPARATUS

CROSS-REFERENCE TO RELATED APPLICATION

This application is a national phase patent application of an International Patent Application under the application number PCT/CN2013/082570 filed Aug. 29, 2013, and the disclosure of which is incorporated herein by reference in its entirety.

FIELD OF THE INVENTION

The present invention relates to an interchangeable multi-purpose healthcare apparatus, which takes advantage of the properties of silicate-based ceramic materials containing tourmaline, corresponds to human body structure, being configured to interconnect with different functional heads with different functions, in order to be a personalized and specialized multi-purpose healthcare apparatus or an auxiliary healthcare apparatus. In particular, the present invention is an interchangeable multi-purpose healthcare apparatus made of silicate-based ceramic materials containing tourmaline, after the multi-purpose healthcare apparatus being added with liquids of different temperatures and shaken vigorously when it is filled with the liquids, far infrared ray emitted and transmitted from the silicate-based ceramic materials containing tourmaline under temperature changes matches microcurrent and negative ions of human bioelectricity, leading to rupture and re-arrangement of molecular groups of the liquids, which result in massage medium or diluted medication. In combination with different types of functional head and auxiliary means, the present invention can become a multi-purpose healthcare apparatus such as a personalized and specialized dilution vessel for homeopathy, massage and scraping therapy.

BACKGROUND

According to a global survey of WHO, those who are genuinely healthy only account for 5%, those who suffer from diseases account for 20%, and those who are under sub-health status account for 75%. One-third of China's population is under sub-health status.

Additionally, according to the 6$^{th}$ Population Census issued by National Bureau of Statistics of China in 2010, the population who were 60 years old and above accounted for 13.26% of the overall national population (178 million), among which the population who were 65 years old and above accounted for 8.87% (119 million). With the development of social aging and improvement of living standards, there will be huge demand of healthcare products.

Since the development and application of tourmaline, it has drawn international attention, and the scope of the application has been gradually extended. At present, major products containing tourmaline include raw ore of various standards, powder of various granularities, various gels, skin care products, textiles containing tourmaline, reductive water and ceramics. The major effects are summarized as follows:

1. Therapeutic effects: Tourmaline products are conducive to curing anemia, psychentonia, autonomic nervous system disorder, edema, anaesthesia, postoperative wound healing, bruise, Burns, Meniere's syndrome, idiopathic dermatitis, Allergies, athlete's foot, dermatitis after mosquito bite, astriction, fear of cold, hyperidrosis, lumbago, cephalagra, dysmenorrhea, headache, arthralgia, scapulohumeral periarthritis, tennis elbow, wrist ache, courbature, sprain, rheumatalgia, flustered and exasperated, asthma, tinnitus, pollinosis, conjunctivitis, asthenopia, teary eyes, dizziness, etc.

2. Improvement of physical fitness and immunity: Tourmaline-containing products are advantageous in improvement of memory, attention focusing, reduction of possibility for catching cold, natural loss of body weight, enhancement of energy, relief of fatigue, promotion of diaphoresis, lipopenia, normal blood pressure and blood sugar, reduction of cholesterol, improvement of body softness, enhancement of explosive power, heightening of sleep quality, improvement of appetite, improvement of vitality, etc.

3. Cosmetic result: Tourmaline products are conducive to blackening of hair, increase of hair, improvement of hair glossiness, no tendency of witheredness, reduction of dandruff, diminishing of baldness, convenience of hair carding, improvement of hair quality; good adhesiveness of cosmetics, with diminishing dosage. Tourmaline products also have the effects of skin beautification and skin whitening, which can make skin smooth, freckle and aestates disappear, and can make skin become soft and elastic.

4. The effects on water: Tourmaline can improve water quality, eliminate the smell of chlorine in tap water and get rid of ozostomia when the treated water is used for gargle. It can replace astringent; fish will grow well in such kind of water; flowers can extend flowering period and refreshing time; water which is treated by tourmaline will enhance its cleaning efficiency, make the vessels more resistant to dirt formation and contamination and become easier for cleaning; it can save water and get rid of dirt when it is used for washing clothes.

5. The effects on air: Tourmaline is capable of purifying air and eliminating odor.

Currently, there are more than 80 countries in the world with the application of homeopathy. 41 of 42 European countries apply homeopathy. According to a statistics, ¾ of Europeans know about homeopathy, 29% of Europeans choose homeopathy, 39% of doctors in France apply homeopathy, which has become favorite therapy for Europeans. Drugs in homeopathy are manufactured by systematic dilutions and succussions. Traditionally dilution vessels for homeopathy are mainly neutral density glass, porcelain and stainless steel ware, so that in the process of dilution the materials for vessels will not be easily have chemical reaction with diluted drugs, but cannot strengthen successions and vitality of diluted drugs.

The drugs for homeopathy are manufactured by a series of systematic dilutions and succussions. Succussions refer to 100 times of forceful successions of diluted liquid which is placed into a glass bottle or porcelain or stainless steel ware. The methods of dilution include: 1) Decimal ratio dilution method; 2) Hahnemann's centesimal ratio dilution method; 3) Korsakoff's centesimal ratio dilution method; 4) 50 times of thousandth ratio dilution method.

In the theory of meridian system, any disease is caused by blocking of meridian system. The only way is to dredge meridian system from the root, so as to make the disease cured naturally. Although it is simple and feasible for independent massage, stimulation of acupuncture points and blocking of meridian system, there is a lack of professional auxiliary apparatus for dredging meridian system and improving habitus, thus this multipurpose health care apparatus is researched and developed.

In Chinese folk tradition, handy articles such as bianstone, ancient copper coin, jade, spoon, wooden comb, toothpick, waste toothbrush, mulberry twig, ball-point pen, pencil or blow dryer are used as auxiliary apparatus for massage, scraping therapy and stimulating acupuncture points. This is the accumulation of civil wisdom, convenient and effective. But after all it is too simple, unprofessional with unitary effect.

Having existed in the market for quite a long time are combs that are normally used in scraping therapy and for stimulating acupuncture points such as bian-stone comb, wooden comb, horn comb and jade comb. Though their effects are genuine, there is no comb in the market which can excrete water carrying negative ions and can combine the mechanism of comb and unique properties of tourmaline in order to exert synergistic effects.

The most popular health care apparatus in the market via meridian points takes advantage of pulse stimulation to cause continuous convulsion and shaking to muscles. It lacks directional and specific health benefits. Its application method is unitary that users can only choose different stimulation frequency and strength. Long-term use and being accustomed to ultra-strong stimulation frequency will cause potential harms to nervous system.

In the market, there are many products via tapping on the meridian system such as health care ball, rolling massager, etc., but they are all unitary in function, in method of application, bulky in size and inconvenient to carry.

The vast majority of health care apparatus in the market only provides physical stimulus but neglects that temperature in fact is the key factor of bringing health. The causes of conditions in certain body parts are due to blocking of vital energy and blood circulation. The slow-down of blood flow (blood stagnation) will lead to a reduction in body temperature. If the meridian system of the affected body parts can be provided with warm and far infrared thermal radiation, it can make blood vessels dilate. In combination with massage, blood stasis can be dissipated, such that the meridian system can be unblocked and our body will be comfortable.

China's Utility Model Patent No. ZL200620067816.7 discloses a type of moxibustion massager but without the disclosure of what materials the massager is made of. It can only be seen from the figures that its structure is relatively complex, and moxa sticks or rolls need to be placed into a control tube followed by inserting the control tube into a tubular handle. Moxa sticks were burnt in the head of the moxibustion massager, where the head was covered with a moxibustion sheath. It can be seen that the space for oxygen supply and ash storage when moxa sticks are burnt is very small, leading to undesirable burning of moxa sticks. Also, the application of protrusion of the moxibustion sheath for massage will easily cause skin burn due to high temperature. In addition, efficacy of medicine and heat will be diffused all around the messager when the moxa sticks are burnt. Furthermore, ordinary consumers have difficulty in managing the distance between the massager and the affected parts such that the skin will easily get burnt if it is too close to the skin while there will be no effect if it is too far away from the skin. In comparison, the structure and application of the present invention are simple and easy-to-use. The burning chamber is configured to have sufficient space for oxygen supply and ash storage. Moreover, it has an additional property of emitting far infrared thermal radiation, and is designed with a fixed direction and distance, such that it is easy for ordinary consumers to use.

There has been no dilution vessel for homeopathy in prior art, which takes advantage of far infrared thermal radiation to create an absorption resonance space that can enhance oscillation of water molecules to make the medicine be well diluted and vitalized.

There has been no generator in prior art, which is portable and compact, and can make water be transformed into healthy drinking water with high wave energy, and can be used as thermos in winter time to provide heat to human body.

There has been no massager with functions of heating and emitting far infrared thermal radiation in prior art, which is portable and convenient for use in dysmenorrhea, so as to make meridian system unblocked again in certain body parts with restoration of vital energy and blood circulation, relieve pains naturally, and make body comfortable.

For initial stage or slight hemorrhoids prolapse, except exterior coating of Chinese patent medicine, the suggested therapy nowadays in western medicine is to soak anus with hot water after evening bath and exercise levator ani. As anus is covered by buttocks and close to reproductive organ, low water temperature has no effect while extremely high water temperature may burn reproductive organ and cause skin burn on buttocks with subcutaneous hemorrhage. Therefore, the effect of such therapy is not significant and it is at high risks. There has been no apparatus in the market and in prior art to cure and relieve hemorrhoids prolapse.

There has been no massager in prior art which has the functions of thermal therapy, emitting far infrared thermal radiation, and transmitting biomicrocurrent and negative ion.

There has been no massager in prior art which can induce a massage medium.

There has been no masturbation device for women in prior art which has the functions of emitting far infrared thermal radiation, transmitting biomicrocurrent and negative ion, providing warm and feeling of body temperature interacting with human microcurrent, and educing egg white analogous to semen.

There has been no moxibustion apparatus in prior art which has directional and specific distance design and the function of emitting far infrared thermal radiation.

There has been no high content negative ion sprayer in prior art which is portable, compact and convenient.

There has been no similar multi-purpose health care apparatus in the market and in prior art which integrates multiple functions and features including light weight and handy volume, portable, simple and practicable, economical and practical, being non-invasive, safe, electricity-free, flexible, without follow-up expenses and maintenance cost.

SUMMARY OF THE INVENTION

The present invention relates to an interchangeable multi-purpose healthcare apparatus, which acts as a generator capable of emitting and transmitting far infrared ray, emitting and transmitting microcurrent and negative ions matching human bioelectricity (0.06 mA), so as to generate heat, far infrared thermal radiation, and as an auxiliary device for unblocking meridian system via emitting biomicrocurrent and negative ions from liquid medium (such as liquid of traditional Chinese medicine, Dieda Wine, fragrant oil, etc.) that directly penetrate into meridian system and acupuncture points. To achieve different purposes, the present multi-purpose healthcare apparatus is configured for connecting with different shapes of heads, which are designed according to different human body structures and functional needs. The present invention can be regarded as a personalized or specialized multi-purpose healthcare apparatus, for example, as a dilution vessel for homeopathy, an apparatus for hemorrhoids prolapse thermal therapy, a device for massage and carding of meridian system and scraping therapy.

The main structure of the present invention is a cylindrical bottle body (FIG. 1), along the cylindrical side of the bottle body is designed with a skirt wing to prevent the healthcare apparatus from rolling and make it stand still in upright position. The bottle body is also designed with a screw-type bottleneck to connect with different functional heads (FIGS. 2, 3, 4, 5, 6, 7). These different functional heads with different designs have different number of micropores used for exudation of liquid medium from the bottle or for spraying or for air circulation and ventilation port of moxibustion.

When the present cylindrical bottle body (FIG. 1) is connected with different functional heads (FIGS. 2, 3, 4, 5, 6, 7), it can perform different functions including but not limited to the followings:

1. Acupuncture massage pen in thermal therapy (FIG. 2);
2. Dilution vessel for homeopathy (FIG. 3);
3. As a generator which is portable and compact, capable of transforming water into healthy drinking water with high wave energy (FIG. 3);
4. Being portable, placed in bosom in winter as thermos (FIG. 3);
5. As a thermal therapy appliance for hemorrhoids prolapse (FIG. 3);
6. As a blunt-end pressure massager in thermal therapy, used for pounding, rubbing, pressing and knocking meridian system (FIG. 3);
7. Scraping therapy, scraping lymph node and vena, which can facilitate unblocking meridian system, dredging lymph and revitalizing skin (FIG. 3);
8. Rubbing face and neck, which can facilitate unblocking meridian system, dredging lymph, revitalizing skin, tightening skin (FIG. 3);
9. Rubbing abdomen in thermal therapy, which can facilitate intestinal tract movement and improve constipation (FIG. 3);
10. Rubbing hypogastrium in thermal therapy, which can relieve menstrual pain (FIG. 3);
11. Rubbing affected parts in thermal therapy, which can relieve back pain, muscular soreness, convulsion, foot cramp, stiff neck, and persistent hiccups caused by diaphragm spasm (FIG. 3);
12. As a masturbation device for women (FIG. 3);
13. As a portable high content negative ion ice water sprayer oxygen bar (FIG. 4);
14. As a moxibustion apparatus which has directional and specific distance design and, function of emitting far infrared thermal radiation (FIG. 5);
15. As a knocking massager in thermal therapy (FIG. 6);
16. As a comb which can emit far infrared thermal radiation for carding of meridian points (FIG. 7).

Working Principle:

The interchangeable multi-purpose healthcare apparatus of the present invention is mainly made of silicate-based ceramics containing tourmaline, which has the following characteristics: 1. It can emit and transmit at normal temperature far infrared ray with a wave length of 4-14 micron and emission rate of 0.92, peak radiation wavelength at surface temperature of 45° C. is 9.1 μm, which is the same as the wavelength of far infrared ray emitted by human body; 2. It can persistently transmit weak electrostatic current (0.06 mA) matching human bioelectricity; 3. It can automatically and permanently release negative ions; 4. It can facilitate release of minerals and trace elements from water such as magnesium, sodium, iron, manganese, lithium, aluminum, boron, silicon, fluorine, hydrogen and oxygen, which are beneficial to human health.

As far infrared ray is a type of heat energy from radiation, the generator and recipient of such need to have the same wavelength in order to generate the effect of radiation resonance. This is analogous to the phenomenon of resonance vibration by rubbing "fish basin". When far infrared ray is with a wavelength of 4-20 micron same as the wavelength of far infrared ray emitted by human body, it is easily absorbed by human body and transformed into internal energy of human body, thereby stimulating vibration of water molecules to generate heat and result in "absorption resonance". When the wavelength of far infrared ray is 4-20 micron and the recipient human body generates "absorption resonance", it can penetrate as deep as 3-5 cm subcutaneously, leading to vibration of water molecules in cells to generate resonance and internal energy which is also absorbed by the human body. Thus, it helps improve blood circulation, revitalize cell tissue, promote metabolism, transfer of nutrients and enzymes, discharge harmful substances accumulated from human body, strengthen immunity, thereby attaining the effect of health care.

The present interchangeable multi-purpose healthcare apparatus is mainly made of silicate-based tourmaline-containing ceramics, which has an electrolytic reaction through contacting with water. Water molecules are hydrolyzed into hydrogen ion with positive charge and oxygen ion with negative charge, i.e. hydroxyl group. Hydrogen ion will immediately be reduced by negative electron released from the ceramics containing tourmaline which becomes hydrogen to be released in the air, while the remaining hydroxyl group reacts with water molecules to form hydroxidion, i.e. negative ion with negative charge. The water in the present interchangeable multi-purpose healthcare apparatus will be slightly alkaline with pH value between 7.4 and 7.6. Meanwhile under the radiation of far infrared ray, macromolecules of water will become micromolecules, so as to strengthen its solubility and seepage force.

The present interchangeable multi-purpose healthcare apparatus is mainly made of silicate-based tourmaline-containing ceramics. It can emit weak electrostatic current (0.06 mA) matching human bioelectricity (0.06 mA), induce biological effect of human bioelectricity, promote metabolism, modulate central nervous system and autonomic nervous system, regulate the functions of cerebral cortex, promote conducive improvement on cardiac rhythm and blood circulation, especially microcirculation. This is a beneficial signal for humoral regulation of cell membrane and cell, especially exchange of ions, energy exchange and information exchange. Specifically, weak electrostatic current (0.06 mA) transmitted by the interchangeable multi-purpose healthcare apparatus has three major benefits to human body: 1.) It can make cell arrangement in order; 2.) It can resist electromagnetic wave harmful to human body; 3.) It can generate beneficial effects on human body by inducing meridian points.

There are five external conditions to exert the effect of tourmaline-containing ceramics: 1. To strengthen the effect by circulation of water and air, since turbulent flow is better than regular flow; 2. To strengthen the effect by temperature change; 3. To strengthen the effect by humidity change, making more contact with water, in order to strengthen electrolytic action and enhance the ability of releasing negative ions; 4. To strengthen the effect by friction; 5. To strengthen the effect by pressure.

Human meridian point is the best window for receiving energy from outside, which can save effort and lead to better result when it is the target of stimulation.

Temperature is the key factor of human survival and health.

In traditional Chinese medicine, it acknowledges that "comb hair on the head can unblock blood vessels". Head is the master of human body, because "the hub of human body connects various meridians". TCM also acknowledges that "Hair is the outcome of blood and elite of kidney". The twelve meridians and eight extra meridians in human body intersect at the head, where there are nearly 50 acupuncture points. The acupuncture points for limbs are distributed in a pattern like the Chinese character "Da" on scalp of human head. Frequent hair combing can exert massage effect on these acupuncture points, which can make meridian system on the head unblocked, improve the communication between meridian system on scalp and various organs of human body, promote enhancement of meridians, smoothening of all meridians, balance of yin yang, leading to the benefits of dredging meridian system, improved circulation of blood and qi, refreshing mind and enlightening. During combing hair, the increase in frequency of contact and friction between the comb teeth and hair can generate electric conduction, induce a type of beneficial stimulation to peripheral nerves on scalp and subcutaneous blood capillary. Through cerebral cortex, nerves at human head can be stretched and relaxed, which is beneficial to modulation of central nervous system, improving blood circulation, improving and enhancing supply of blood oxygen in scalp and brain cells, eliminating brain fatigue, strengthening brain function, making people think more quickly with good memory, so as to decelerate aging of brain. Regular combing may also benefit in prevention of cold, high blood pressure, cerebral arteriosclerosis, cerebral apoplexy, and senile dementia, etc. The unblocking of meridian system and improved circulation of oxygenated blood may also eliminate headache immediately. As proven by clinical studies, combing hair has beneficial effects on preventing tension-type headache, nerve headache, migraine, prosopalgia, hypertension headache and neurasthenia headache. Through nervous reflex action, gentle stimulation by combing hair can promote blood circulation of head, speed up metabolism of cells, enhance supply of blood oxygen to scalp and hair and make hair become glossy. As proven by modern research, regular combing and massaging has six major advantages: (1) It can dredge blood vessels, which is beneficial to blood circulation in brain, enhancement of memory and prevention of senile dementia; (2) It can make hair to obtain sufficient nutrients, prevent baldness and early greying, which generally improves hair quality; (3) It can dispel heat, prevent cold and relieve headache; (4) It is useful in improving eyesight, reducing high blood pressure and preventing the occurrence of cerebrovascular diseases; (5) It can strengthen brain and refresh one's mind, relieve mental stress, improve sleep and eliminate fatigue; (6) It is beneficial to metabolism and coordination of central nervous system, leading to longer and healthier lifespan.

DETAILED DESCRIPTION OF PREFERRED EMBODIMENTS

Figure 1:
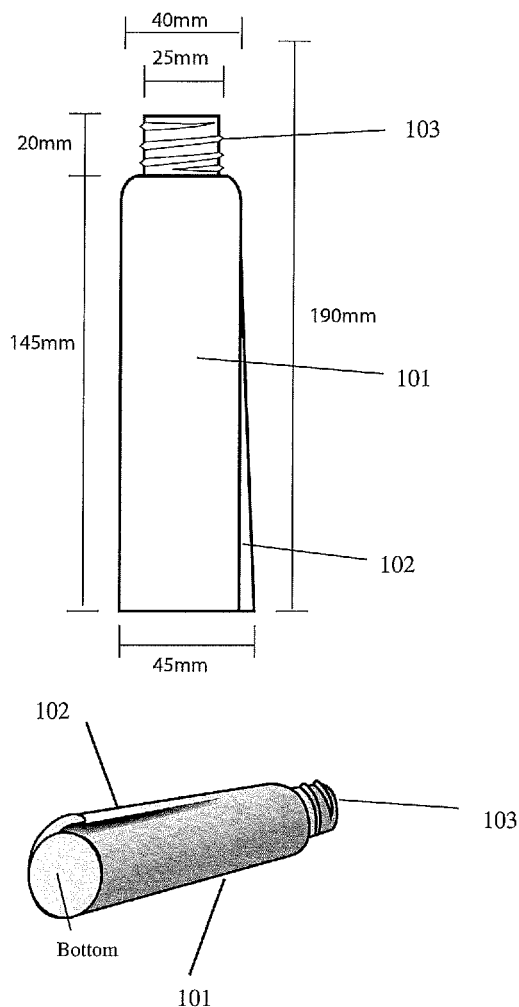
FIG. 1 is a diagram illustrating main body structure of the interconnetable multi-purpose healthcare apparatus of the present invention.

The present invention relates to an interchangeable multi-purpose healthcare apparatus, which has the properties of emitting and transmitting far infrared ray, serves as a generator of microcurrent and negative ions which match human bioelectricity (0.06 mA), and is also capable of transducing heat to meridian system and acupuncture points in order to serve as an auxiliary device for unblocking meridian system. In some embodiments (FIGS. 1, 2, 3, 6, 7), the present invention is shown to have multi-functions of thermal therapy with needling, pounding, rubbing, pressing, knocking of acupuncture points of meridian system; scraping therapy, such as scraping lymph gland and vena; rubbing face and neck for beautification and dredging lymph. Other embodiment (FIG. 5) is a moxibustion apparatus which has directional and specific distance design and capable of emitting and transmitting far infrared thermal radiation. Another embodiment (FIG. 4) is a high-content negative ion water sprayer. Yet another embodiment (FIG. 3) is an apparatus for thermal therapy which can be portable and placed in bosom in winter as thermos. Further embodiment (FIG. 3) provides that the present invention can also be used as masturbation device for women and dilution vessel in homeopathy.

In one embodiment, before connecting with different functional heads, hot water or liquid is added into the main body of the interchangeable multi-purpose healthcare apparatus (the cavity of the bottle body 101 shown in FIG. 1), followed by connecting the top open end of the main body with different functional heads (as shown in FIGS. 2, 3, 6, 7) and screwing down the functional head towards a top open end which is a screw-type bottleneck until the functional head tightly closes the top open end of the main body of the apparatus. After that, the apparatus is shaken vertically or along the same axis of the bottle body, making the heat from the hot water or liquid rapidly and evenly distributed throughout the entire apparatus. Far infrared emission from the apparatus is activated by the temperature change and vigorous vibration of the water or liquid in the cavity of the main body of the apparatus. Under the effects of the far infrared radiation and bumping force induced by the vigorous vibration of water, the molecular group of hot water is restructured and thereby forming smaller water molecular groups. Meanwhile, under thermo-electric effect and piezoelectric effect, more microcurrents are generated, which results in a stronger negative ion effect in water. Different functional heads are designed with micropores according to functional needs, where the micropores which are narrow inside and broad outside have a rubber stopper and cover in order to make the present apparatus serve as a portable thermal bottle and to prevent water from spilling out when shaking before use. Slow exudation of far infrared irradiated and negatively ionized water, liquid of traditional Chinese medicine or Dieda Wine inside the apparatus can act as a medium for pressing skin in thermal therapy. Firstly, the medium has lubrication effect. Secondly, the medium can enhance surface moisture content of the healthcare apparatus and further stimulate the generation of far infrared ray, microcurrent and negative ions in the presence of the pressure exerted during massage. Thirdly, the medium can enable direct penetration of active ingredient from the liquid of traditional Chinese medicine or the liquid itself with high content of negative ions via meridian points to human body. In addition, the heat from the wall of the bottle of the healthcare apparatus together with thermal radiation of the far infrared ray increases the surface temperature of the apparatus. The heat from the surface of the apparatus can thereby be transmitted subcutaneously to muscles, making capillary blood vessels and lymph vessels dilate. Body fluid and molecular groups in blood can be dissociated into smaller molecules under thermal radiation of the far infrared ray, so as to improve blood circulation. Under assistance by external pressure from different massage techniques as above mentioned by applying the healthcare apparatus of the present invention, the waste accumulated in systemic circulation system will be discharged, so as to dredge meridian system and ameliorate or eliminate conditions.

FIG. 1 shows the basic structure of the present multipurpose healthcare apparatus. The cylindrical bottle body is the container of main body of the healthcare apparatus which is configured with a screw-type bottleneck 103 at a top open end for connecting with different functional heads (FIGS. 2, 3, 4, 5, 6, 7). After adding hot/cold water into the inner cavity of the cylindrical bottle body, the top open end of the cylindrical bottle body is connected with different functional heads (FIGS. 2, 3, 4, 6, 7) and screw down the functional head corresponding to the screw-type bottleneck until the functional head closes the top end of the cylindrical bottle body tightly. The apparatus is then vigorously shaken in vertical direction to increase friction of the water inside the inner cavity with the inner wall of the bottle body, generating more water sprays and breaking water into smaller molecules. The cylindrical bottle body 101 in FIG. 1 is further configured with a protruding skirt wing 102 for use in scraping therapy including but not limited to scraping meridian system and scraping lymph and for preventing the present healthcare apparatus from rolling and for making it to stand still in upright position. The remaining cylindrical bottle wall surface can be used for rubbing face and neck. When the present healthcare apparatus is used for massage, the heat and thermal radiation of far infrared ray can be transmitted into meridian system and acupuncture points through the bottle wall.

Figure 2:
FIG. 2 is a schematic diagram showing a functional head after which connects with the main body of the interchangeable multi-purpose healthcare apparatus to serve as an acupuncture massage pen in thermal therapy according to an embodiment of the present invention.

FIG. 2 shows an embodiment of which the present invention is used as acupuncture massage pen in thermal therapy. The tip of the functional head is designed with a micropore 203. Before the pen-shaped functional head 201 is connected with the cylindrical bottle body of the present apparatus through an inner thread 202 of the functional head, hot water or liquid of traditional Chinese medicine is added into the cavity of the cylindrical bottle body (bottle body 101 shown in FIG. 1). After closing the top end of the cylindrical bottle body by moving the inner thread of the functional head along the screw-type bottleneck of the cylindrical bottle body, the bottle is vertically shaken to stimulate emission and transmission of far infrared ray, microcurrents and negative ions matching human bioelectricity. When the pen tip is being pressed on and slides on acupuncture points, it induces exudation of negatively ionized hot water or liquid of traditional Chinese medicine and transmits weak electrostatic current (0.06 mA) matching human bioelectricity; minerals and trace element such as magnesium, sodium, iron, manganese, lithium, aluminum, boron, silicon, fluorine, hydrogen and oxygen, which are beneficial to human health, together with the induced exudation of negatively ionized hot water or liquid of traditional Chinese medicine, will penetrate into meridian points and conduct ion exchange and information exchange through meridian system. Therefore, human meridian point is the best window for receiving energy from outside, which can save effort and lead to better result.

Figure 3:
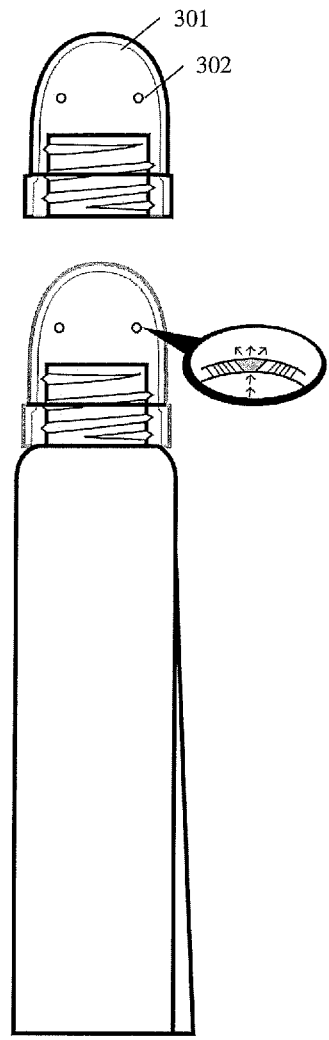
FIG. 3 is a schematic diagram showing a functional head and after which connects with the main body of the interchangeable multi-purpose healthcare apparatus to serve as an dilution vessel for homeopathy and as blunt-end pressure massager in thermal therapy according to an embodiment of the present invention.

FIG. 3 shows an embodiment of the present cylindrical bottle body (bottle body 101 shown in FIG. 1) being added with a ready-to-dilute medication, hot water or other massage medium used in homeopathy (such as fragrant oil, Dieda Wine, liquid of traditional Chinese medicine or honey egg white water). The front end of a bullet-shaped functional head 301 is configured with two micropores 302 which can regulate the volume of water flow by press pressure, where the micropores which are narrow inside while are broad outside have a rubber stopper and cover in order to enable the present apparatus as a portable thermal bottle and to prevent water from spilling out during shaking before use. It can be used for multiple purposes and accomplish multiple effects of healthcare and physical therapy, including but not limited to:

1. As a dilution vessel in homeopathy: By connecting the cylindrical bottle body (bottle body 101 shown in FIG. 1) which is filled with the ready-to-dilute medication used in homeopathy with the corresponding functional head, and then screwing down the functional head towards the screw-type bottleneck until the functional head closes the top open end of the bottle tightly, followed by vigorously shaking the bottle up and down for about 200 times, the liquid in the bottle is poured out until only one unit volume of liquid remains in the bottle. 100 unit volume of alcohol is then added into the bottle followed by vigorous shaking vertically for 200 times to form a first diluent, i.e. 1K or 1CK diluent. The above process is repeated to prepare 2K and 3K diluents. This is suitable for domestic application and for personal preparation of some simple and commonly-used homeopathy medications.

2. As a generator for healthy drinking water with high wave energy: By connecting the cylindrical bottle body (bottle body 101 shown in FIG. 1) which is filled with hot water with the corresponding functional head, and then screwing down the functional head towards the screw-type bottleneck until the functional head closes the top open end of the bottle tightly, followed by vigorously shaking the bottle up and down, hot water in the bottle is rapidly being negatively ionized and the molecular groups thereof are broken down and rearranged. This can rapidly remove odors from water and make it smooth in taste with ionic energy.

3. Being portable and placed in bosom as thermos in winter time: By connecting the cylindrical bottle body (bottle body 101 shown in FIG. 1) which is filled with hot water with the corresponding functional head, and then screwing down the functional head towards the screw-type bottleneck until the functional head closes the top open end of the bottle tightly, followed by vigorously shaking the bottle up and down, also by taking advantage of the present invention which is capable of emitting and transmitting far infrared ray with the same wave length as that of human body, a radiation resonance is therefore generated such that when it can be placed in bosom, the feeling of heat is not limited to the body part which is in contact with the bottle surface. When the hot water is cooled down to suitable temperature, the water becomes the healthy drinking water with high wave energy as in the foregoing example suitable for direct drinking, and then be replaced by a new round of hot water, which does not waste the water and is convenient.

4. As an apparatus for initial stage or slight hemorrhoids prolapse in thermal therapy: haemorrhoids refers to soft vena groups formed by extending and bending of venae plexus below terminal mucosa of rectum and anal canal skin; hemorrhoids prolapse is mainly composed of extended vena, spongy tissue and mesenchyme of connective tissue. When vena extends and bends, blood vessel wall becomes thinner, outer membrane and middle lamella shrink, elastic tissue becomes less elastic. Thrombus may be formed inside the vena, and blood clot may also be formed outside the vena. For the time being, by removing the rubber stopper and cover of the micropores 302 at the functional head 301, it allows negatively ionized hot water to flow out through the bottle wall from the cavity of the bottle. The functional head 301 is turned upside down, and then the bottle connected with the functional head is clamped firmly between buttocks, and the negatively ionized hot water continues to flow out and moisten the area of hemorrhoids prolapse. With the emission and transmission of far infrared thermal radiation from the bottle matching the wavelength of the far infrared ray generated by human body, it results in radiation resonance. Heat transmitted through the bottle wall and along with the effluent hot water will penetrate subcutaneously in 3-5 cm deep under the skin, making water molecules in cells to generate resonance and internal energy which can be absorbed by human body, thereby dilating the artery and increasing blood circulation. Under the effect of far infrared ray, large and aging molecular groups in body fluid and blood become smaller molecule groups, which results in smaller resistance to blood flow. In addition, contaminants (e.g. $CO_2$, $SO_2$, $CL_2$, etc.) on the surface of water molecule groups are eliminated, blood cholesterol level in blood vessels is thereby decreased, leading to reduction in blood viscosity, blood flow quicken, capillaries extend, so as to naturally unblock the channel of microcirculation, gradually relieve and reduce hemorrhoids prolapse.

5. Used as a blunt-end pressure massager in thermal therapy: By connecting the cylindrical bottle body (bottle body 101 shown in FIG. 1) which is filled with pre-heated massage medium with the corresponding functional head, and then screwing down the functional head towards the screw-type bottleneck until it closes the top open end of the bottle tightly, the present apparatus becomes an apparatus used in thermal therapy, i.e. blunt-end pressure massager in thermal therapy. It can replace finger, tip of the elbow, or first back for pounding, rubbing, pressing and knocking meridian system. This is suitable for use as "original point therapy" to replace the therapy which relies on finger force to search for pain spots and presses on those pain spots, especially suitable for most women or for whom are insufficient in finger force. This can also prevent the practitioner from finger joint sprain caused by long-term forceful pressing and rubbing. Except the typical use in massage, by further removing the rubber stopper and cover of the micropores 302 which covers the functional head (FIG. 3), the negatively ionized fragrant oil, Dieda Wine or liquid of traditional Chinese medicine as massage medium can be exuded through the two micropores 302 on the functional head which can regulate the volume of water flow by pressing, thereby conducting ion exchange and information exchange through meridian system.

6. Used in scraping therapy, for scraping lymph gland and vena: By connecting the cylindrical bottle body (bottle body 101 shown in FIG. 1) which is filled with pre-heated massage medium with the corresponding functional head, and then screwing down the functional head towards the screw-type bottleneck until it closes the top open end of the bottle tightly, the present apparatus becomes an apparatus used in thermal therapy, i.e. an apparatus for scraping therapy, scraping lymph gland and vena. The protruding skirt wing 102 of the cylindrical bottle body (bottle body 101 shown in FIG. 1) can be used to scrape on lymph gland or vena. The negatively ionized fragrant oil, Dieda Wine or liquid of traditional Chinese medicine as massage medium can be exuded through the two micropores 302 on the functional head which can regulate the volume of water flow by pressing, thereby conducting ion exchange through meridian system. Thus, this can lead to unblocking meridian system, attaining the positive effects of dredging lymph and activating body and skin.

7. Used for rubbing face and neck: By connecting the cylindrical bottle body (bottle body 101 shown in FIG. 1) which is filled with pre-heated massage medium with the corresponding functional head, and then screwing down the functional head towards the screw-type bottleneck until it closes the top open end of the bottle tightly, the present apparatus becomes an apparatus for skincare in thermal therapy. In this example, the cylindrical bottle body (bottle body 101 shown in FIG. 1) can be used to rub face and neck. Through the two micropores 302 on the functional head which can regulate the volume of water flow by pressing, the negatively ionized fragrant oil, Dieda Wine or liquid of traditional Chinese medicine as massage medium is exuded from the micropores to conduct ion exchange via meridian system. Tourmaline-containing products have the positive effects on skincare and skin whitening due to the properties of tourmaline, which can make the skin becomes smoother, eliminate freckle and aestates, make the skin softer and more elastic. It can also facilitate unblocking of meridian system, revitalizing and tightening the skin.

8. Used for rubbing abdomen in thermal therapy, which facilitates peristalsis and curing of constipation: By connecting the cylindrical bottle body (bottle body 101 shown in FIG. 1) which is filled with pre-heated massage medium with the corresponding functional head, and then screwing down the functional head towards the screw-type bottleneck until it closes the top open end of the bottle tightly, followed by vigorously shaking the bottle up and down, the protruding skirt wing (skirt wing 102 shown in FIG. 1) of cylindrical bottle body (bottle body 101 shown in FIG. 1) can be used to scrape on abdomen regularly from top to bottom and from one side to the other; or to scrape abdomen clockwise by centering on belly button. Through the two micropores 302 on the front which can regulate the volume of water flow by pressing, the negatively ionized hot water, fragrant oil, or liquid of traditional Chinese medicine as massage medium can be exuded from the micropores to conduct ion exchange via meridian system. This can effectively relieve mental stress, improve sleep and eliminate fatigue.

9. Used for rubbing hypogastrium in thermal therapy, which can relieve menstrual pain: By connecting the cylindrical bottle body (bottle body 101 shown in FIG. 1) which is filled with pre-heated massage medium with the corresponding functional head, and then screwing down the functional head towards the screw-type bottleneck until it closes the top open end of the bottle tightly, followed by vigorously shaking the bottle up and down, the cylindrical bottle body (bottle body 101 shown in FIG. 1) can be used to rub hypogastrium in thermal therapy. Through the two micropores 302 on the functional head which can regulate the volume of water flow by pressing, the negatively ionized hot water, fragrant oil, or liquid of traditional Chinese medicine as massage medium under negative ionization can be exuded from the micropores to conduct ion exchange through meridian system. Since tourmaline-based ceramics has the positive effects on pain relief and anti-inflammation, together with the positive effects of the heat and the far infrared thermal radiation transmitted from the bottle wall surface of the cylindrical bottle body (bottle body 101 shown in FIG. 1), it makes the present apparatus an ideal healthcare apparatus for relieving menstrual pain.

10. Used for treating muscle spasm, convulsion, stiff neck, persistent hiccups caused by diaphragm spasm in thermal therapy: By connecting the cylindrical bottle body (bottle body 101 shown in FIG. 1) which is filled with pre-heated massage medium with the corresponding functional head, and then screwing down the functional head towards the screw-type bottleneck until the functional head closes the top open end of the bottle tightly, followed by vigorously shaking the bottle up and down, the cylindrical bottle body (bottle body 101 shown in FIG. 1) can be used to rub the body parts with spasm, convulsion or stiff neck. Through the two micropores 302 on the functional head which can regulate the volume of water flow by pressing, the negatively ionized hot water, fragrant oil, or liquid of traditional Chinese medicine as massage medium can be exuded from the micropores to conduct ion exchange through meridian system. This can effectively relieve back pain, muscular soreness, convulsion, foot cramp, stiff neck, and persistent hiccups caused by diaphragm spasm.

11. As a masturbation device for women: By connecting the cylindrical bottle body (bottle body 101 shown in FIG. 1) which is filled with pre-heated massage medium at body temperature with the corresponding functional head, and then screwing down the functional head towards the screw-type bottleneck until the functional head closes the top open end of the bottle tightly, followed by vigorously shaking the bottle up and down. Through the two micropores 302 on the functional head which can regulate the volume of water flow by pressing, honey egg white, warm fragrant oil analogous to prostatic fluid and semen as massage medium which are negatively ionized can be exuded from the micropores to conduct ion exchange and information exchange through the most sensitive nerve endings. Firstly, the apparatus looks like a male penis after connecting the functional head 301 (FIG. 3) with the cylindrical bottle body (bottle body 101 shown in FIG. 1). Secondly, because the interchangeable multi-purpose healthcare apparatus is capable of emitting and transmitting microcurrent matching human bioelectricity, there can be an exchange of bioelectricity during eye closure when the apparatus slightly touches the most sensitive part of human body. Thirdly, the bottle wall surface of the apparatus can be adjusted to body temperature, leading to the user's imagination that she is in a sexual contact with opposite sex. Fourthly, the apparatus can be directly added with warm honey egg white, or warm water with fragrant oil. Through the two micropores 302 on the functional head which can regulate volume of water flow by pressing, the medium exuded from the microspores mimics prostatic fluid and semen as a friction medium, which enhances biofidelity. Fifthly, since thermal radiation effect of far infrared ray can lead to vasodilation, increase blood flow, make pudenda and clitoris swell with blood and erect, make engorged and tight nerve endings of skin surface become more sensitive, so as to obtain pleasant sensation and climax in the process. This is suitable for the disabled or widows who cannot be satisfied in normal sexual life to regain satisfaction through the enjoyment provided by the present apparatus.

Figure 4:
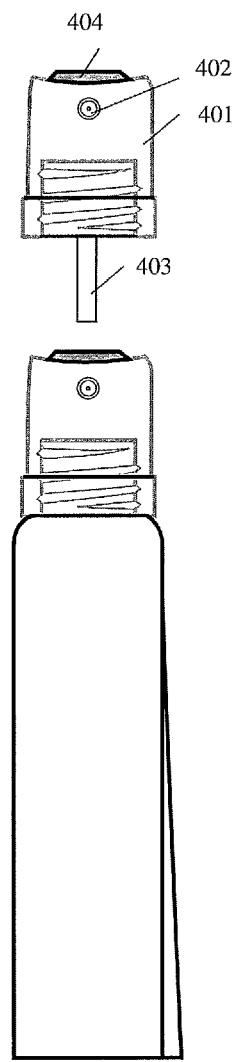
FIG. 4 is a schematic diagram showing a functional head and after which connects with the main body of multipurpose health care apparatus to serve as a high-content negative ion-containing water sprayer according to an embodiment of the present invention.

FIG. 4 shows the structure of the present invention according to an embodiment which is used as a high content negative ion ice water sprayer when the cylindrical bottle body (bottle body 101 shown in FIG. 1) of the present apparatus is connected with the corresponding functional head. The functional head is a sprayer 401 which is a press-type device, wherein the front end thereof includes at least a nozzle 402, a pressing valve 404, a sucker 403 extended from the nozzle towards an inner hollow part of said functional head until the inner cavity of said cylindrical bottle body. There is a circular baffle in the front of the nozzle. The sprayer's inner wall is configured with spiral thread, which corresponds to the spiral thread on the screw-type bottleneck of said cylindrical bottle body and is used for connecting said sprayer with said cylindrical bottle body by screwing down the sprayer until it closes the top open end at the bottleneck tightly, making said interchangeable multi-purpose healthcare apparatus become a type of high content negative ion sprayer. The sprayer 401 makes the nozzle 402 first spray water at high speed to the baffle followed by reflecting back by the baffle to form a plurality of smaller water spots under atomization, leading to formation of a space with high content of negative ions. Ice water is added into the cylindrical bottle body (bottle body 101 shown in FIG. 1) of the multi-purpose healthcare apparatus, followed by connecting the bottle with the sprayer 401, screwing down the sprayer until it tightly connects with the bottleneck, and then the bottle is vigorously shaken up and down. Owing to the temperature difference from room temperature and piezoelectric effect, the far infrared thermal radiation and microcurrent are generated, and ice water is negatively ionized, leading to smaller molecular groups of the water. Water spray on the face in hot summer can not only immediately make people feel cool, relieve summer heat and make temperature drop, smaller molecular groups with high content of negative ions after atomization can also become a portable oxygen reservoir, and small water spots attached on the face has a positive effect on tightening skin.

Figure 5:
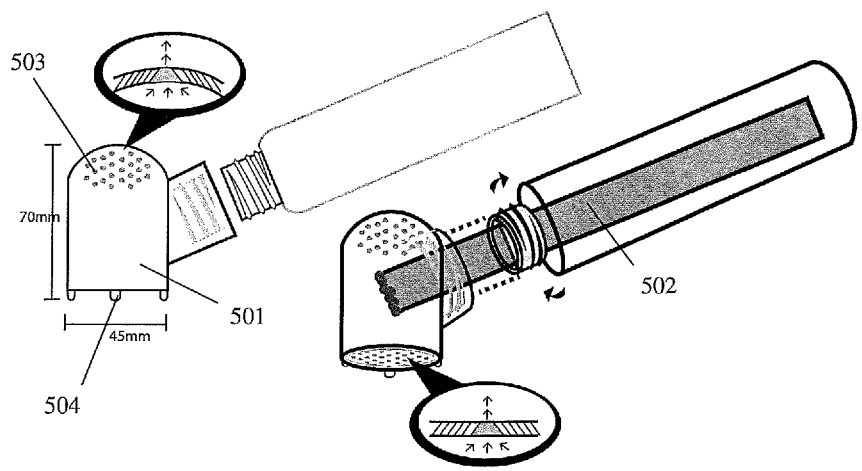
FIG. 5 is a schematic diagram showing a cylindrical and arch-shaped functional head and after which connects with the main body of the interchangeable multi-purpose healthcare apparatus to serve as a moxibustion apparatus according to an embodiment of the present invention.

FIG. 5 shows the structure of the present invention used as a cylindrical moxibustion combustor with an arch-shaped head. First of all, moxa stick 502 is lit and put into the cylindrical bottle body (bottle body 101 shown in FIG. 1) which serves as a handle. The igniting end of the moxa stick is exposed to connect into a moxibustion combustor 501, and then secure the connection by screwing down the moxibustion combustor through the spiral thread at where the moxa stick is exposed towards the screw-type bottleneck of the cylindrical bottle body. The top and bottom ends of the moxibustion combustor 501 are respectively configured with a plurality of trumpet-shaped micropores 503 having broad base and narrow tip for convection and ventilation. The design of the micropores allows suitable and sufficient amount of fresh air to smoothly flow into the moxibustion combustor. The efficacy of the medication and heat generated during the combustion of the moxa stick are therefore retained in the combustor. In combination with the effect of far infrared thermal radiation, the active ingredients of the medication and heat generated penetrate into meridian system of affected parts through the trumpet-shaped micropores situated at the bottom end of the moxibustion combustor. Since the trumpet-shaped micropores at the bottom end of the combustor are broad at the base and narrow at the tip, it avoids moxa ash after combustion to fall onto the skin and cause burn. The bottom of the moxibustion combustor is configured with a thermal insulation foot pad 504, of which one purpose is for forming air passage to allow fresh air to smoothly flow into the combustor through the trumpet-shaped micropores at the bottom of the combustor. Other purpose of having the thermal insulation foot pad is for providing a fixed distance between the bottom of the combustor and the skin during the combustion of the moxa stick in order to avoid burning of the skin. Thus, the present apparatus integrates both the active ingredients of the medication and heat generated during the combustion of the moxa stick through the incorporation of the micropores and thermal insulation structure into the moxibustion combustor which is a directional and specific distance design while having the property of emitting and transmitting far infrared thermal radiation in order to effectively enhance the effect of moxibustion on the skin of the user.

Figure 6:
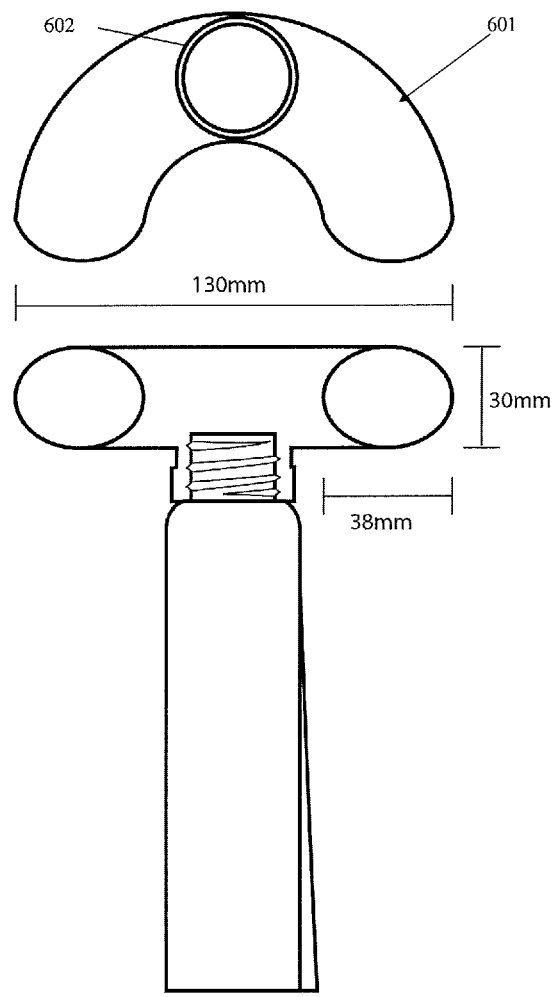
FIG. 6 is a schematic diagram showing a functional head and after which connects with the main body of the interchangeable multi-purpose healthcare apparatus to serve as a knocking massager in thermal therapy according to an embodiment of the present invention.

FIG. 6 shows an embodiment of the present invention which is used as a knocking massager in thermal therapy. Firstly, the cylindrical bottle body (bottle body 101 shown in FIG. 1) which is filled with hot water is connected with the corresponding functional head. After screwing the functional head down towards the screw-type bottleneck until it closes the top open end of the bottle tightly, the apparatus can not only be used for knocking meridian system but also for massaging the principal meridian at the back. The U-shaped functional head is a knocking massager 601 which is configured with spiral thread at a circular opening 602 at the bottom side in the middle of the U-shaped functional head. The functional head vertically connects with the cylindrical bottle body (bottle body 101 shown in FIG. 1) by screwing down through the circular opening towards the screw-type bottleneck of the cylindrical bottle body in order to form a 7-shaped or rakelike apparatus. At the end of two arms of the U-shaped functional head, it is respectively configured with a narrow-inside and broad-outside micropores. After the bottle is filled with hot water and the top open end of the bottle is closed tightly by the functional head, the bottle is then shaken vigorously up and down. When the apparatus is used for knocking meridian system, the water in the bottle body is forced to flow into the interior of two arms of the U-shaped functional head due to centrifugal force exerted during shaking the bottle, such that the inertia so generated during knocking can save force applied by the user. The water continuously flowing back and forth in the apparatus when it is in use for knocking further stimulates the generation of microcurrent, negative ion and far infrared ray. The narrow-inside and broad-outside micropores are covered by a rubber stopper and cover, which can prevent water from splashing out during water filling and shaking before use.

Figure 7:
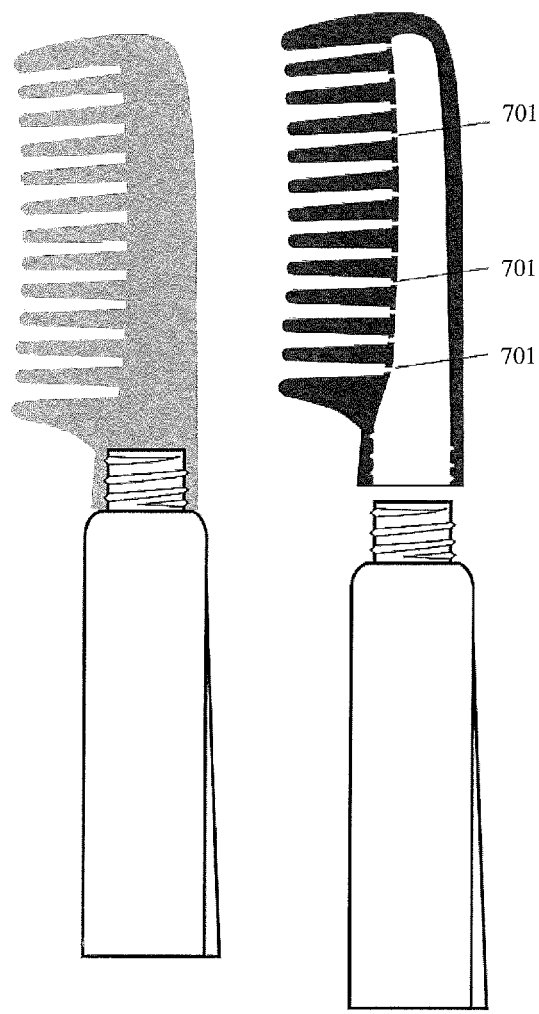
FIG. 7 is a schematic diagram showing a functional head and after which connects with the main body of the interchangeable multi-purpose healthcare apparatus to serve as a comb for carding meridian points according to an embodiment of the present invention.

FIG. 7 shows the structure of the present invention which is used as a comb for carding meridian points having property of emitting far infrared thermal radiation. By connecting the cylindrical bottle body (bottle body 101 shown in FIG. 1) which is filled with hot water or warm fragrant oil with the corresponding functional head, and then screwing down the functional head towards the screw-type bottleneck until the functional head closes the top open end of the bottle tightly, followed by vigorously shaking the bottle up and down. Through a plurality of micropores 701 at the bottom of the comb tooth, the negatively ionized hot water as massage medium is exuded from the micropores. During carding, frequent contact and friction between the comb teeth and hair can generate electric induction. Moreover, the present apparatus can emit and transmit microcurrent matching human bioelectricity, which is a beneficial stimulus to peripheral nerves on scalp and subcutaneous blood capillary, and conduct ion exchange and information exchange through the nerve endings. Through cerebral cortex, scalp nerve can be stretched and relaxed, which facilitates modulation of nervous centralis, improvement in blood circulation, improving and enhancing supply of blood oxygen to scalp and brain cells, eliminating brain fatigue, strengthening brain function, making people thick more quickly, and improve memory so as to postpone aging of brain. The twelve meridians and eight extra meridians in human body intersect at the head, where there are nearly 50 acupuncture points. Carding hair actually enables the carding of meridian system. For those who suffer from diseases or disorders associated with gall bladder meridian blocking such as headache or sick cholecyst, hyperplasia of mammary glands should have corresponding blocking spots in meridians at the head. Meridian system is interconnected, what is blocked at other parts of human body has corresponding blocking spot in meridians at the head. In addition, the unique positive effects of the present apparatus containing tourmaline include the following benefits: blackening of hair, increase in hair growth, improvement of hair glossiness, no tendency of witheredness, reduction of dandruff, diminishing of baldness, convenience of hair carding, improvement in hair quality. In addition, the present invention combs meridian points for improving body fitness. According to meridian system theory in traditional Chinese medicine, among the 12 most important meridians, six of them are associated with hands. There are 23 related acupuncture points and 34 extra points on hands. By massaging or pressing these acupuncture points, it can cure almost the diseases of the whole body. Therefore, the negatively ionized warm fragrant oil as massage medium is exuded from the micropores at the bottom of the comb tooth to the palm of the hand, followed by combing on the palm vertically and horizontally, then as a circle in clockwise direction, and then repeat the procedure once in a reverse order. Following this method to massage every day can achieve the goal of body fitness and disease curing. The present invention can also be used to comb meridian points to enhance the breast health. Combing breast is a simple and effective method to prevent diseases and keep breast fit. Clinical studies support that combing breast can increase its blood circulation, enhance secretion of mammary gland and discharge silting-up milk. It has additive therapeutic effects on postpartum hypogalactia, latex fill up, mammary pain, acute mastitis and hyperplasia of mammary glands. Even if there is no disease in female breast, regular carding can make it fit. For adolescent girls who comb breast by the present invention, it can promote normal growth of the breast. Postnatal women who regularly comb breast by the present invention can keep breast strong and plump. It is suggested to comb from the bottom of breast to the surrounding of the papilla, then comb from the bottom of breast to the papilla in circular motion, for once a day and for about five minutes at each time.

In conclusion, the interchangeable multi-purpose healthcare apparatus of the present invention adopts the theory of meridian system which includes the views that any disease is caused by blocking of meridian system, temperature is the key factor of human survival and health, and human meridian point is the best window for receiving energy from outside. It combines the properties of silicate-based ceramic materials containing tourmaline and positive effects of tourmaline-containing products on effective treatment, improvement of habitus and immunity, beauty care, skin whitening, improvement of hair quality, etc. The present invention is configured for purifying water and air, and attaining various beneficial effects.

INDUSTRIAL APPLICABILITY

The present invention integrates the theory of meridian system which includes the views that any disease is caused by blocking of meridian system, temperature is the key factor of human survival and health, and human meridian point is the best window for receiving energy from outside into the multi-purpose healthcare apparatus, which is configured by combining the properties of silicate-based ceramic materials containing tourmaline and various positive effects thereof. The present interchangeable multi-purpose healthcare apparatus can almost satisfy the healthcare needs of the whole body. Moreover, it has the advantages of light in weight and handy volume, portable, wide application, simple and practicable, economical and practical, while it can save follow-up expenses and maintenance cost, being non-invasive, safe in use, no need of electricity, being safe and flexible. In nowadays society where there is an increasing awareness of personal health, a type of multi-purpose healthcare apparatus for, dredge meridian system which can address the root problem while relieve symptoms or conditions is urgently in need by the general public.

The invention claimed is:

1. An interchangeable multi-purpose healthcare apparatus made of silicate-based ceramic materials containing tourmaline, the apparatus comprising a cylindrical bottle body and a functional head, wherein:

a top end of said cylindrical bottle body is configured with a screw-type bottleneck to connect with said functional head;

said functional head comprises one or more micropores configured for exudation of liquid medium negatively ionized from an inner cavity of the cylindrical bottle body or for spraying or as a ventilation channel for moxibustion; and said silicate-based ceramic materials containing tourmaline are capable of emitting and transmitting far infrared rays, microcurrent and negative ions at a certain temperature, where the microcurrent matches human bioelectricity.

2. The apparatus of claim 1, wherein said functional head is screwed down towards the screw-type bottleneck.

3. The apparatus of claim 1, wherein one side of a cylindrical wall of said cylindrical bottle body is configured with a protruding wing.

4. The apparatus of claim 1, wherein said functional head is pen-shaped, the pen-shaped functional head comprising a tip, and the one or more micropores being located at the tip, such that the apparatus is configured to be an acupuncture massage pen.

5. The apparatus of claim 1, wherein said functional head is bullet-shaped, such that said apparatus is configured to be a blunt-end pressure massager.

6. The apparatus of claim 1, wherein said functional head is configured to be a press-type spraying device, the press-type spraying device comprising a nozzle, a pressing valved, a sucker extended from the nozzle to an inner cavity of said cylindrical bottle body.

7. The apparatus of claim 1, wherein said functional head is configured to be a cylindrical moxibustion combustor with an arch-shaped head.

8. The apparatus of claim 7, wherein the cylindrical moxibustion combustor comprises one or more foot pads.

9. The apparatus of claim 1, wherein said functional head is U-shaped.

10. The apparatus of claim 1, wherein said functional head is comb-shaped such that the apparatus is configured to be a comb.

* * * * *